United States Patent [19]

Papenfhus et al.

[11] Patent Number: 5,545,768

[45] Date of Patent: * Aug. 13, 1996

[54] PROCESS FOR THE PREPARATION OF CHLOROFLURONITROBENZENES AND DIFLUORONITROBENZENES

[75] Inventors: Theodor Papenfhus, Frankfurt am Main; Andreas Kanschik-Conradsen, Gernsheim/Rhein; Wilfried Pressler, Kelkheim/Taunus, all of Germany

[73] Assignee: Hoechet AG, Germany

[*] Notice: The portion of the term of this patent subsequent to Oct. 31, 2012, has been disclaimed.

[21] Appl. No.: 958,107

[22] PCT Filed: Jun. 8, 1991

[86] PCT No.: PCT/EP92/01079

§ 371 Date: Dec. 22, 1992

§ 102(e) Date: Dec. 22, 1992

[87] PCT Pub. No.: WO91/00270

PCT Pub. Date: Jan. 9, 1992

[30] Foreign Application Priority Data

Jun. 25, 1990 [DE] Germany .................. 40 20 130.9
Aug. 31, 1990 [DE] Germany .................. 40 27 591.4

[51] Int. Cl.$^6$ ................................ C07C 205/12
[52] U.S. Cl. .................. 568/938; 568/937; 570/127; 570/141; 570/142; 570/170; 570/182; 570/206
[58] Field of Search ................ 570/141, 142, 570/127, 206, 170, 182; 568/938, 937

[56] References Cited

U.S. PATENT DOCUMENTS

| | | | |
|---|---|---|---|
| 3,064,058 | 11/1962 | Duesel | 568/937 |
| 3,240,824 | 3/1966 | Boudakian et al. | 568/937 |
| 3,992,432 | 11/1976 | Napier et al. | 558/344 |
| 4,140,719 | 2/1979 | Tull et al. | 556/70 X |
| 4,164,517 | 8/1979 | Fuller | 568/938 |
| 4,287,374 | 9/1981 | North | 568/937 |
| 4,642,239 | 2/1987 | Cantrell | 568/937 |
| 4,642,399 | 2/1987 | White | 568/938 |
| 4,780,559 | 10/1988 | Brown et al. | 568/938 X |
| 4,849,552 | 7/1989 | Cantrell | 568/937 |
| 4,978,769 | 12/1990 | Kysela et al. | 558/423 |
| 5,081,288 | 1/1992 | Blank et al. | 570/147 |
| 5,463,148 | 10/1995 | Papenfuhs et al. | 568/938 |
| 5,476,976 | 12/1995 | Papenfuhs et al. | 568/938 |

OTHER PUBLICATIONS

Chem. Abs. 111:57247a Jan. 17, 1989.
Chen, W., *Chem. Abs.* 113:15 200g (1990).

*Primary Examiner*—Sharon Gibson
*Assistant Examiner*—Valerie Fee
*Attorney, Agent, or Firm*—Connolly & Hutz

[57] ABSTRACT

A process for the preparation of chlorofluoronitrobenzenes and difluoronitrobenzenes, which comprises heating dichloronitrobenzene to not more than 200° C. in excess with an alkali metal fluoride having a total water content of about 0.2 to about 2.5% by weight in the presence of a quaternary ammonium and/or phosphonium salt, crown ether and/or polyethylene glycol dimethyl ether as catalyst in the absence of a solvent.

13 Claims, No Drawings

PROCESS FOR THE PREPARATION OF CHLOROFLURONITROBENZENES AND DIFLUORONITROBENZENES

The present invention relates to a process for the preparation of chlorofluoronitrobenzenes and difluoronitrobenzenes in high yields without additional purification operations by reaction of an excess of the appropriate dichloronitrobenzenes with alkali metal fluorides of a certain water content in the presence of catalysts and in the absence of a solvent.

Chlorofluoronitrobenzenes and difluoronitrobenzenes are important intermediates for the preparation of pharmaceuticals and plant protection agents.

U.S. Pat. No. 4,164,517 describes the reaction of 3,4- and 2,4-dichloronitrobenzene to give chlorofluoro- or difluoronitrobenzenes using predried potassium fluoride in sulfolane at temperatures above 200° C. The yield can be increased here by increasing the proportion of sulfolane. The fact that, in the reaction of 2,4-dichloronitrobenzene without sulfolane, only 20% is converted even after a reaction time of 30 h at 240° C. is thus explained.

A process for the preparation of monofluoronitrobenzenes from, in particular, monochloronitrobenzenes using finely powdered potassium fluoride in the melt at preferably 140° to 150° C. with the addition of tetraalkyl- or aralkylammonium salts as catalysts is described in U.S. Pat. No. 4,287,374. The reaction times here according to the examples are 17 to 28 h. The disadvantages of this process, apart from the poor space-time yield, are to be seen in the fact that the potassium fluoride preferably used has a water content of less than 0.2% by weight, which makes pretreatment of the potassium fluoride necessary.

There was therefore a considerable interest in an industrially more favorable process for the preparation of chlorofluoronitrobenzenes and difluoronitrobenzenes.

It has now surprisingly been found that chlorofluoronitrobenzenes and difluoronitrobenzenes can be prepared in high yields by heating dichloronitrobenzene to not more than 200° C. in molar excess with an alkali metal fluoride having a total water content of about 0.2 to about 2.5% by weight in the presence of a quaternary ammonium and/or phosphonium salt, crown ether and/or polyethylene glycol dimethyl ether as catalyst in the absence of a solvent.

In the process according to the invention, it is particularly important that thorough mixing of the reaction suspension is ensured during the entire reaction time.

The reaction temperature can vary within a range from about 125° to about 200° C.; the temperatures, however, between about 140° and about 190° C. are expediently chosen as in this case, on the one hand, the rate of reaction is satisfactory and, on the other hand, the catalyst remains relatively stable.

Catalysts which can be used are quaternary ammonium compounds, in particular tetraalkyl($C_1$ to $C_{22}$)-ammonium halides, tetraarylammonium halides, it being possible for the aryl radicals to be, for example, phenyl or naphthyl radicals which can be substituted by halogen atoms or branched or unbranched alkyl, nitro, cyano, amino and/or alkoxy groups, and mixed alkylarylammonium halides, such as octadecyltrimethylammonium chloride, distearyldimethylammonium chloride, tetramethylammonium chloride, tetramethylammonium bromide, hexadecyltrimethylammonium chloride; benzyltrimethylammonium bromide; quaternary phosphonium compounds, in particular tetraalkyl($C_1$ to $C_{22}$)-phosphonium halides, tetraarylphosphonium halides, it being possible for the aryl radicals to be, for example, phenyl or naphthyl radicals which can be substituted by halogen atoms or branched or unbranched alkyl groups, nitro, cyano, amino and/or alkoxy groups, and mixed alkylarylphosphonium halides such as stearyltributylphosphonium bromide or hexadecyltriethylphosphonium bromide; crown ethers, such as 18-crown-6, polyethylene glycol dimethyl ether and combinations of these, in catalytic amounts. The catalyst was employed in the process according to the invention in amounts of about 2 to about 10% by weight, preferably of about 3 to about 5% by weight, relative to dichloronitrobenzene.

Alkali metal fluorides which can be employed are lithium fluoride, sodium fluoride, potassium fluoride, rubidium fluoride, cesium fluoride or combinations of these, potassium fluoride and cesium fluoride being preferred.

Suitable dichloronitrobenzenes are, for example, 3,4-dichloronitrobenzene, 2,5-dichloronitrobenzene, 2,3-dichloronitrobenzene and 2,4-dichloronitrobenzene, which can be converted into the corresponding chlorofluoro- or difluoronitrobenzenes.

As far as the amount ratio of dichloronitrobenzene to alkali metal fluoride is concerned, expediently about 1.05 to about 1.7 mol of dichloronitrobenzene are reacted with 1 mol of alkali metal fluoride. The dichloronitrobenzene, however, can also be used in a molar excess of up to 5:1. By the use of the dichloronitrobenzene in excess, the yield of chlorofluoro- or difluoronitrobenzene can be substantially increased. Moreover, it is thereby ensured that the suspension does not become too viscous and thus still remains stirrable.

The process according to the invention is customarily carried out at atmospheric pressure. However, it is also possible to work at elevated pressure, for example at up to 25 atm.

It is of particular advantage in the process according to the invention that neither the dichloronitrobenzenes and alkali metal fluorides employed nor the catalyst used have to be additionally dried, and that the use of a solvent can be dispensed with.

The examples below are used to illustrate the invention without restricting it thereto.

EXAMPLES 1. 70 g (0.2 mol) of octadecyltrimethylammonium chloride were dissolved in a melt of 2020 g (10.5 mol) of 3,4-dichloronitrobenzene at 50° C. with stirring, 580 g (10.0 mol) of potassium fluoride were suspended at 100° C. and this suspension was heated to 180° C. for 9 h. After cooling to about 60° C., the reaction suspension was filtered with suction, the liquid adhering to the residue was distilled off at 150° C./70 torr and the combined organic phases were fractionated with the addition of an auxiliary base as an acid scavenger. 1445 g (90.6%, relative to 3,4-dichloronitrobenzene converted) of 3-chloro-4-fluoronitrobenzene and 324 g (13.6%, relative to 3,4-dichloronitrobenzene employed) of unreacted 3,4-dichloronitrobenzene were obtained.

2. 2020 g (10.5 mol) of 2,5-dichloronitrobenzene, 70 g (0.2 mol) of octadecyltrimethylammonium chloride and 580 g (10.0 mol) of potassium fluoride were reacted analogously to Example 1. 936 g (72.3%, relative to 2,5-dichloronitrobenzene converted) of 2-fluoro-5-chloronitrobenzene and 600 g (29.7%, relative to 2,5-dichloronitrobenzene employed) of unreacted 2,5-dichloronitrobenzene were obtained.

3. 576 g (3 mol) of 3,4-dichloronitrobenzene, 58 g (0.1 mol) of distearyldimethylammonium chloride and 139 g (2.4 mol) of potassium fluoride were reacted analogously to Example 1. After filtering with suction, the residue was dissolved in water, the organic phase was separated off and the combined organic phases were fractionated. 289 g (69%, relative to potassium fluoride employed) of 3-chloro-4-fluoronitrobenzene were obtained.

4. 96 g (0.5 mol) of 3,4-dichloronitrobenzene were reacted with 68 g (0.45 mol) of cesium fluoride and 8 g of distearyldimethylammonium chloride at 180° C. After 4 h, the conversion was over 70% (GC) with the formation of 3-chloro-4-fluoronitrobenzene.

5. 96 g (0.5 mol) of 3,4-dichloronitrobenzene were reacted with 26 g (0.45 mol) of potassium fluoride and 4 g of distearyldimethylammonium chloride and 4 g of tetraethylene glycol dimethyl ether at 180° C. After 4 h, the conversion was over 50% (GC) with the formation of 3-chloro-4-fluoronitrobenzene.

6. 101 g (0.53 mol) of 2,3-dichloronitrobenzene were reacted with 29 g (0.5 mol) of potassium fluoride and 5 g of tetrabutylphosphonium bromide at 180° C. After 19 h, the conversion was over 65% (GC) with the formation of 2-fluoro-3-chloronitrobenzene.

7. 96 g (0.5 mol) of 3,4-dichloronitrobenzene were reacted with 26 g (0.45 mol) of potassium fluoride and 7 g of polyethylene glycol dimethyl ether 1000 at 200° C. After 19 h, the conversion was 37% (GC) with the formation of 3-chloro-4-fluoronitrobenzene.

8. 96 g (0.5 mol) of 3,4-dichloronitrobenzene were reacted with 26 g (0.45 mol) of potassium fluoride and 1.7 g of 18-crown-6 at 180° C. After 21 h, the conversion was 83% (GC) with the formation of 3-chloro-4-fluoronitrobenzene.

9. 96 g (0.5 mol) of 3,4-dichloronitrobenzene were reacted with 23 g (0.4 mol) of potassium fluoride and 4 g of stearyltributylphosphonium bromide and 0.8 g of 18-crown-6 at 180° C. After 16 h, the conversion was 72% (GC) with the formation of 3-chloro-4-fluoronitrobenzene.

10. 96 g (0.5 mol) of 3,4-dichloronitrobenzene were reacted with 28 g (0.45 mol) of potassium fluoride/cesium fluoride in the ratio 9:1 and 8 g of benzyltrimethylammonium bromide at 180° C. After 21 h, the conversion was over 70% (GC) with the formation of 3-chloro-4-fluoronitrobenzene.

11. 202 g (1.1 mol) of 2,3-dichloronitrobenzene were reacted with 56 g (1.0 mol) of potassium fluoride and 10 g of tetramethylammonium chloride at 180° C. After 19 h, the conversion was over 70% (GC) with the formation of 3-chloro-2-fluoronitrobenzene.

12. 202 g (1.1 mol) of 2,3-dichloronitrobenzene were reacted with 56 g (1.0 mol) of potassium fluoride and 10 g of tetramethylammonium bromide at 180° C. After 19 h, the conversion was over 70% (GC) with the formation of 3-chloro-2-fluoronitrobenzene.

13. 101 g (0.53 mol) of 2,4-dichloronitrobenzene were reacted with 58 g (1.0 mol) of potassium fluoride and 5 g of hexadecyltriethylphosphonium bromide at 180°0 C. After 21 h, the conversion was over 65% (GC) with the formation of 2,4-difluoronitrobenzene.

We claim:

1. A process for the preparation of a chlorofluorinitrobenzene or a difluoronitrobenzene which comprises:

heating a dichloronitrobenzene, in excess and in the essential absence of solvent, to a reaction temperature of not more than 200° C. with an alkali metal fluoride having a total water content of about 0.2 to about 2.5% by weight, in the presence of, as a catalyst, a quaternary ammonium or quaternary phosphonium salt or a crown ether or polyethylene glycol dimethyl ether or a mixture thereof.

2. The process as claimed in claim 1, wherein:

said quaternary ammonium salt is a tetra-$C_1$-$C_{22}$-alkylammonium halide or a tetra-substituted or unsubstituted-arylammonium halide, and said crown ether is 18-crown-6.

3. The process as claimed in claim 1, wherein:

said quaternary phosphonium salt is a tetra-$C_1$-$C_{22}$-alkylphosphonium halide, a tetra-substituted or unsubstituted-arylphosphonium halide, a mixed alkylarylphosphonium halide, or a mixture thereof, and said crown ether is 18-crown-6.

4. The process as claimed in claim 1, wherein the catalyst is at least one of the following compounds selected from the group consisting of octadecyltrimethylammonium chloride, distearyldimethylammonium chloride, tetramethylammonium chloride, tetramethylammonium bromide, hexadecyltrimethylammonium chloride, benzyltrimethylammonium bromide, stearyltributylphosphonium bromide, and hexadecyltriethylphosphonium bromide.

5. The process as claimed in claim 1, wherein said catalyst is present in the amount of about 2 to about 10% by weight, relative to the amount of dichloronitrobenzene.

6. The process as claimed in claim 5, wherein said amount of catalyst is about 3 to about 5% by weight, relative to the amount of dichloronitrobenzene.

7. The process as claimed in claim 1, wherein about 1.05 to about 1.7 mole of dichloronitrobenzene is reacted with each mole of alkali metal fluoride.

8. The process as claimed in claim 1, wherein the alkali metal fluoride is selected from the group consisting of potassium fluoride, cesium fluoride, and a mixture thereof.

9. The process as claimed in claim 1, wherein the dichloronitrobenzene, the alkali metal fluoride, and the catalyst are reacted essentially in the form in which they have been obtained, without additionally drying.

10. The process as claimed in claim 1, wherein said reaction temperature is about 125° to about 200° C.

11. The process as claimed in claim 1, wherein said reaction temperature is about 140° to about 190° C.

12. The process as claimed in claim 1, wherein said process is carried out at atmospheric pressure or at elevated pressure.

13. The process as claimed in claim 12, wherein said process is carried out at atmospheric pressure.

* * * * *

UNITED STATES PATENT AND TRADEMARK OFFICE
CERTIFICATE OF CORRECTION

PATENT NO.  : 5,545,768
DATED       : August 13, 1996
INVENTOR(S) : Papenfuhs et al It is certified that error appears in the above-indentified patent and that said Letters Patent is hereby corrected as shown below:

On the face of the patent, the Patentees name should read -- Papenfuhs et al --.

Item [75] Inventors:, "Papenfhus" should read --Papenfuhs--.

Item [73] Assignee:, "Hoechet" should read --Hoechst--.

Item [86] PCT No:, "PCT/EP92/01079" should read --PCT/EP91/01079--.

Item [87] PCT Pub. No.:, "WO91/00279" should read --WO92/00270--.

Signed and Sealed this

Eighth Day of April, 1997

Attest:

BRUCE LEHMAN

Attesting Officer          Commissioner of Patents and Trademarks